United States Patent [19]

Park et al.

[11] Patent Number: 5,569,598
[45] Date of Patent: Oct. 29, 1996

[54] **EXTRACELLULAR AMINOPEPTIDASE ISOLATED FROM *STREPTOCOCCUS THERMONITRIFICANS* CULTURE**

[75] Inventors: Soon J. Park; Young M. Lee; Teug Y. Won; Soon C. Kwon; Seung J. Lee; Jung H. Kim; Bum J. Kim, all of Daejeon, Rep. of Korea

[73] Assignee: Lucky Limited Co., Seoul, Rep. of Korea

[21] Appl. No.: 261,525

[22] Filed: Jun. 17, 1994

[30] Foreign Application Priority Data

Jun. 17, 1993 [KR] Rep. of Korea .................. 93-11107

[51] Int. Cl.⁶ .................. C12N 9/48; C12N 9/52; C12N 1/20
[52] U.S. Cl. .................. 435/212; 435/220; 435/252.35
[58] Field of Search .................. 435/212, 220, 435/252.35

[56] References Cited

U.S. PATENT DOCUMENTS

| 4,146,432 | 3/1979 | Hirohara et al. ............ 435/180 |
| 5,143,839 | 9/1992 | Blumberg et al. ............ 435/220 |

FOREIGN PATENT DOCUMENTS 0204527 12/1986 European Pat. Off. .

| 8601229 | 2/1986 | WIPO . |
| 8604609 | 8/1986 | WIPO . |
| 8805993 | 8/1988 | WIPO . |

OTHER PUBLICATIONS

Aphale et al. (1993)*J. Gen. Microbiol.*, 139(3), "Purification and properties of an extracellular aminopeptidase from *Streptomyces lividans* 1326", pp. 417–424.
A. Spungin & S. Blumber Eur. J. Biochem., 183, 471–477.
Lj. Vitale, et al. Appl. Microbiol. Biotechnlol., 23, 449–455.
T. Uwajima, et al. Agr. Biol. Chem., 37(12), 2727 (1973).
K. D. Vosbeck, et al. J. Biol. Chem., 248, 6029–6034 (1973).

*Primary Examiner*—David M. Naff
*Assistant Examiner*—Jon P. Weber
*Attorney, Agent, or Firm*—Anderson, Kill & Olick P.C.

[57] ABSTRACT

An extracellular leucine aminopeptidase was isolated from the culture medium of Streptomyces thermonitrificans which is a $Zn^{2+}$-dependent metalloenzyme which comprises an amino acid sequence Lys-Phe-Ser-Lys-Lys-Phe-Asn-Glu (SEQ ID NO: 3) at the N-terminal thereof, and amino acid sequences of Glu-Pro-Gly-Thr-Gly-Ala-Leu-Glu-Pro (SEQ ID NO: 4) and Asn-Pro-Asp-Ile-Val-Tyr (SEQ ID NO: 5) at other regions thereof. The aminopeptidase has a pH optimum of 7.5 to 9.0, a temperature optimum of 30° to 50° C., and an apparent molecular weight as determined by sodium dodecyl sulfate polyacrylamide gel electrophoresis under reducing conditions of 41 to 45 kDa, and as determined by gel filtration under native state conditions of 36 to 40 kDa.

3 Claims, 10 Drawing Sheets

EXTRACELLULAR AMINOPEPTIDASE ISOLATED FROM *STREPTOCOCCUS THERMONITRIFICANS* CULTURE

FIELD OF THE INVENTION

The present invention relates to a novel aminopeptidase and a process for the preparation thereof. More particularly, it pertains to a novel aminopeptidase separated from a culture of *Streptomyces thermonitrificans;* a process for producing said aminopeptidase by culturing said microorganism; and a process for preparing a wild-type recombinant protein by using said aminopeptidase.

BACKGROUND OF THE INVENTION

Aminopeptidases are found in various microorganisms and animal cells, and generally metallo-proteases requiring a metal ion such as calcium and zinc for their activities. Said enzymes are known to be capable of maintaining their activities of diverse nature, depending on their origin of derivation, even in a temperature range of 50° to 70° C.

Aminopeptidases have their industrial uses in the determination of protein primary structures, and in the pharmaceutical drug development etc., and, in particular, they are useful for the preparation of a recombinant protein having a same amino acid sequence as its wild-type protein by eliminating N-terminal methionine from the recombinant protein, which is accompanied by methionine in its N-terminal(N-methionyl recombinant protein), produced in a microorganism by using a recombinant DNA technique.

As the presence of an N-terminal methionine on recombinant human proteins may cause an unwanted immune reaction when administered to human beings, it would be desirable to remove the N-terminal methionine, thus producing the mature eucaryotic proteins whose primary amino acid sequences are identical to that of human origin.

G. Roncari and H. Zuber disclosed in *Method in Enzymology,* 19, 544(1970) three aminopeptidases derived from *Bacillus stearothermophilus,* having slightly different properties from each other; and Takayuri Uwajima et al. reported in *Agr. Biol. Chem.,* 37(12), 2727(1973) the physicochemical properties of an aminopeptidase requiring a calcium ion for maintaining its activity, which was derived from *Streptomyces peptidofaciens* KY 2389.

In addition, various aminopeptidases have been obtained from, e.g., *Bacillus subtilis* (Fred W. Wagner et al., *Arch. Biochem. Biophys.,* 197(1), 63–72(1979)), *Streptomyces rimosus* (Lj. Vitale et al., *Appl. Microbiol. Biotechnol.,* 23, 449–455(1986)), *Streptomyces griseus* (K. D. Vosbeck et al., *J. Biol. Chem.,* 238, 6029–6034(1973)), etc.

A. Spungin and S. Blumberg disclosed in *Eur. J. Biochem.,* 183, 471–477(1989) an aminopeptidase having a molecular weight of about 33 kd as determined by SDS-PAGE and N-terminal amino acid sequence of Ala-Pro-Asp-Ile-Pro-Leu (SEQ ID NO: 1), which was separated and purified by a process which comprises heat-treating a culture of *Streptomyces griseus* separated from soil and subjecting the heat-treated culture to Bio-Gel P-4 gel filtration chromatography and DEAE Sepharose ion exchange chromatography.

Recently, an enzyme called pronase, separated from *Streptomyces griseus* K-1 strain, has become commercially available. However, since the enzyme contains various proteinases as a mixture, it is not efficient to remove only the N-terminal methionine residue.

On the other hand, there have been many attempts made to prepare a wild-type protein by removing the N-terminal methionine residue from the recombinant protein produced in a microorganism. Exemplary methods thereof may include a process for preparing wild-type human growth hormone by expressing a fusion protein in which the N-terminal of human growth hormone is fused with the C-terminal of another protein, and then severing the fusion protein by using a specific protease(PCT International Publication No. WO 89/12678; EP Patent Publication Nos. 20290 and 321940); a process for preparing a wild-type recombinant protein by expressing a recombinant protein having a secretion signal peptide in a microorganism cell so that the secretion signal peptide containing the N-terminal methionine residue is removed when the protein is secreted out of the cell and then recovering the wild-type recombinant protein from the medium (EP Laid-open Publication No. 0088632 A2; U.S. Pat. No. 4,755,465; Japanese Patent Laid-open Publication No. 01273591; EP Patent Publication No. 306673; and Korean Patent Laid-open Publication No. 94-579). However, the above methods produce a low yield, have the difficulty of isolating the desired wild-type recombinant protein from the fusion protein if the two proteins have similar physical properties, and may require complicated and laborious procedures for transforming a host cell with a newly prepared expression vector and determining the optimum fermentation conditions.

It has been suggested that a wild-type recombinant protein may be prepared without suffering from such defects by using a specific aminopeptidase which is capable of specifically removing a methionine residue present in its N-terminal of N-methionyl recombinant protein(PCT International Publication Nos. WO 86/04609 and WO 86/204527 A1). For example, in the case of methionyl human growth hormone whose N-terminal amino acid sequence is Met-Phe-Pro-Thr-Ile (SEQ ID NO: 2), the N-terminal methionine may be removed selectively by using an aminopeptidase which can recognize the X-pro(wherein X means any amino acid residue) site at the N-terminal, thereby terminating its severing reaction before the X residue.

Hitherto, a limited number of aminopeptidases such as the one separated and purified from a culture of *Vibrio proteolyticus*(Bio-Technology General Corp., WO 86/01229) and the one extracted and purified from a porcine kidney (Takeda, WO 86/204527 A1) have been reportedly used for the preparation of a wild-type recombinant protein by removing its N-terminal methionine residue. However, there still exists a demand for the development of aminopeptidases which meet various substrate specificity and high enzyme activity requirements.

SUMMARY OF THE INVENTION

Accordingly, it is an object of the present invention to provide a novel aminopeptidase derived from a culture of *Streptomyces thermonitrificans.*

Another object of the present invention is to provide a process for producing said aminopeptidase by way of culturing *Streptomyces thermonitrificans.*

An additional object of the present invention is to provide a process for preparing a wild-type recombinant protein by removing the N-terminal methionine residue from its N-methionyl recombinant protein by using said aminopeptidase.

BRIEF DESCRIPTION OF DRAWINGS

The above and other objects and features of the present invention will become apparent from the following description of the invention taken in conjunction with the accompanying drawings, in which.

DETAILED DESCRIPTION OF THE INVENTION

Figure 1:
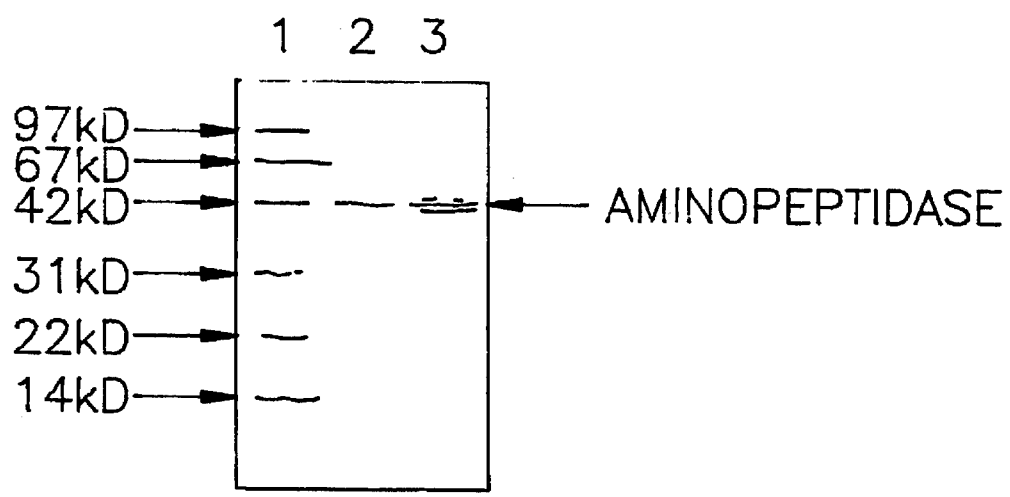
FIG. 1 shows the result of SDS polyacrylamide gel electrophoresis(SDS-PAGE) for determining the molecular weight the aminopeptidase separated from the culture of *Streptomyces thermonitrificans;*

All references cited herein are hereby incorporated in their entirety by reference.

The novel aminopeptidase of the present invention has a molecular weight of about 41 to 45 kd when measured on a SDS-polyacrylamide gel(i.e., in a reduced state) and about 36 to 40 kd when measured by a gel filtration chromatography (i.e., in its natural state).

The aminopeptidase comprises the amino acid sequence of Lys-Phe-Ser-Lys-Lys-Phe-Asn-Glu (SEQ ID NO: 3) at its N-terminal and the amino acid sequences of Glu-Pro-Gly-Thr-Gly-Ala-Leu-Glu-pro (SEQ ID NO: 4) and Asn-Pro-Asp-Ile-Val-Tyr (SEQ ID NO: 5) in other regions; and it can be classified as a leucine aminopeptidase since it reacts specifically with leucine but reacts restrictively to positively-charged amino acids such as lysine.

The aminopeptidase of the present invention exhibits a high activity at a pH ranging from 7.5 to 9.0, more preferably, from 8.0 to 8.5, and at a temperature ranging from 20° to 70° C., more preferably, from 30° to 50° C., and maintains its activity at, e.g., 50° C. for several hours.

Further, the aminopeptidase is a metallo-protease since its activity is increased by the presence of a divalent metal ion such as zinc and magnesium and is diminished when the metal ion forms a complex with a chelating agent such as orthophenanthroline.

The aminopeptidase of the present invention is prepared by culturing *Streptomyces thermonitrificans.* The amount of the aminopeptidase which can be obtained may vary with the kind and the concentration of carbon source in the culture medium. Galactose is preferably employed as the carbon source at a concentration ranging from 1 to 5% by weight, preferably, from 2 to 3% by weight on the basis of the total weight of the medium.

The formulation of the medium except for the employment of galactose as the carbon source and the condition for culturing *Streptomyces thermonitrificans* may be adjusted in accordance with conventional procedures described in, e.g., *FEMS Microbiol. Lett.,* 40, 61–66(1987) by C. Edwards and A. S. Ball. After the cultivation is completed, the culture is centrifuged to obtain the supernatant thereof; ammonium sulfate is added to the supernatant to the concentration of 20 to 60% (weight/volume) by weight, preferably 30 to 50% (wt/vol); the supernatant containing ammonium sulfate is subject to a triphase partition (R. Lovrien et al., *Protein purification Micro to Macro,* Alan R. Liss, Inc., New York, pp 131–148(1987)) by adding tertiary butanol to the supernatant having an appropriate concentration of ammonium sulfate to obtain a clear solution as a lower layer thereof (first triphase partition); to the clear solution is added ammonium sulfate to a concentration ranging from 70 to 100% (wt/vol), preferably from 80 to 90% (wt/vol), and the resultant is repeatedly subjected to the triphase partition procedure to partition and obtain an intermediate layer, containing the desired protein, between the tertiary butanol layer(upper phase) and the aqueous layer(lower phase) in the form of aggregates(second triphase partition); and the intermediate layer is dissolved in a buffer and subjected to cation exchange chromatography employing, e.g., S-sepharose column and FPLC(Fast Performance Liquid Chromatography: Pharmacia, Sweden) employing, e.g., FPLC mono-S column, so as to obtain the aminopeptidase in a high degree of purity.

The aminopeptidase of the present invention can be used for preparing a wild-type recombinant protein. An N-methionyl recombinant protein produced in a microorganism, e.g., E. coli, is reacted with the aminopeptidase under an optimal condition in an appropriate reaction buffer, e.g., a buffer consisting of 50 mMTris(pH 8.0), 100 NaCl, 2%, and 1 mM PMSF, to remove the N-terminal methionine therefrom.

The aminopeptidase of the present invention may be reacted with an N-methionyl recombinant protein prepared from a host cell, such as E. coli and yeast, to obtain the wild-type recombinant protein by removing the N-terminal methionine therefrom. The aminopeptidase can be employed in an appropriate amount determined by considering the molecular weight and the concentration of the N-methionyl recombinant protein; and, in case of an N-methionyl human growth hormone, 0.2 to 20 units of the aminopeptidase may be employed per mg of the growth hormone.

The reaction buffer, e.g., Tris-HCl, employed for the removal of N-terminal methionine may have a pH ranging from 7.5 to 9.5, preferably from 8 to 8.5; and a concentration of NaCl ranging from 0 to 300 mM, preferably from 0 to 100 mM.

The reaction may be carried out at a temperature ranging from 20° to 50° C., preferably from 30° to 40° C. for 10 to 20 hours.

The following Examples are intended to further illustrate the present invention without limiting its scope; and the experimental methods used in the Examples can be practiced in accordance with the Reference Example given hereinbelow, unless otherwise stated.

Further, percentages given below for solids in solid mixtures, liquids in liquids and solids in liquids are on a wt/wt, vol/vol and wt/vol basis, respectively, unless specifically indicated otherwise.

REFERENCE EXAMPLE

The activity of an aminopeptidase was determined in accordance with the method of Pfleiderer as described in *Meth. Enzymol.*, 19, 514–521(1970).

To 1 ml of a buffer(100 mMTris, pH 8.0) containing 20 μl of 25 mg/ml leucine-paranitroanilide(Sigma, USA) solubilized in 50% DMSO(dimethylsulfoxide, Sigma, USA) as a substrate was added a fixed amount of an aminopeptidase. The resulting solution was reacted at 37° C. for 1 minute, and then, the optical density thereof at 405 nm($OD_{405nm}$) was measured. 1 unit of aminopeptidase activity was defined as the amount of the enzyme which was capable of increasing $OD_{405nm}$ by 1.

Example 1: Change of Aminopeptidase Productivity According to the Kind of a Carbon Source in a Medium The following experiment was carried out to determine the effect of a carbon source on the production of the aminopeptidase in a culture of *Streptomyces thermonitrificans*(ATCC 23385).

1 ml of *Streptomyces thermonitrificans*(ATCC 23385) mycelium suspended in seed stock medium containing 25%(vol/vol) glycerol, 1.0% peptone, 0.5% casamino acid, 0.55% potassium phosphate dibasic, 0.05% potassium phosphate monobasic and 3.0% D-galactose to a concentration of 10 to 30% by wet cell weight was inoculated into mediums containing 1.0% peptone, 0.5% yeast extract and 2.0% of a carbon source selected from the group consisting of glucose, galactose, mannose, lactose and sucrose, respectively; and then cultured at 50° C. 1 ml of each of the cultures was taken at 19, 24 and 39 hours, respectively, and centrifuged at 13,000 xg for 5 minutes to obtain the supernatant thereof.

The activity of the aminopeptidase present in each supernatant was determined on the basis of the activity obtained by culturing said microorganism in a medium containing galactose as a carbon source for 39 hours, being 100%. The results are shown in Table 1 below.

TABLE 1

Activity of the aminopeptidase in 1 ml of the culture cultivated with various carbon sources

| cultivation period(hours) | glucose | galactose | mannose | lactose | sucrose |
|---|---|---|---|---|---|
| 19 | 4.7 | 48.4 | 26.4 | 14.7 | 12.8 |
| 24 | 48.4 | 58.9 | 37.6 | 35.3 | 25.2 |
| 39 | 15.5 | 100.0 | 45.0 | 22.1 | 22.1 |

Example 2: Culture of *Streptocyces Thermonitrificans*

To produce the novel aminopeptidase of the present invention by culturing *Streptomyces thermonitrificans*, the following procedures were carried out.

Into a 1 l flask was added 300 ml of a sterilized seed-culture medium(final pH of 7.4 to 7.6) containing 2.0% galactose, 1.0% trypton, 0.5% casamino acid, 0.6% phosphate, 0.01% $MgSO_4$, 0.01% $FeCl_2$, 0.01% $MnCl_2$ and 0.01% $ZnCl_2$. 1 ml of *Streptomyces thermonitrificans*(ATCC 23385) mycelium suspended in seed stock medium containing 25%(vol/vol) glycerol, 1.0% peptone, 0.5% casamino acid, 0.55% potassium phosphate dibasic, 0.05% potassium phosphate monobasic and 3.0% D-galactose to a concentration of 10 to 30% by wet cell weight was inoculated into the above sterilized medium and then cultured at 50° C. for 20 hours as a seed culture.

Into each of four 5 l fermenters were added 3 l of a sterilized culture medium(final pH of 7.4 to 7.6) containing 3.0% galactose, 0.3% trypton, 0.3% casamino acid, 1.4% skim milk, 0.6% phosphate, 0.01% $MgSO_4$, 0.01% $FeCl_2$, 0.01% $MnCl_2$ and 0.01% $ZnCl_2$. 70 ml of the seed culture obtained above was inoculated into each of the above sterilized medium and then cultured for 18 to 22 hours maintaining an agitation speed of 500 rpm, a temperature of 50° C. and an aeration rate of 1 vvm.

Example 3: Purification of the Aminopeptidase

The purified aminopeptidase was obtained from the culture of Example 2 in accordance with the following procedures:

About 10 l of the culture obtained in Example 2 was centrifuged at 10,000 xg for 30 minutes with a centrifuge(JA10 rotor, Beckman, U.S.A.) to obtain the supernatant thereof. The supernatant was passed over a Amicon spiral cartridge (molecular weight cut-off: 10 kd, Amicon, U.S.A.) to concentrate it to a volume of 2 l.

100% ammonium sulfate solution was added to the concentrate to a final concentration of 33%, the equal volume of tertiary butanol was added thereto and the resulting solution was stirred for 1 hour. The resultant was centrifuged at 10,000 xg for 10 minutes to obtain a clear solution as a lower layer thereof(first triphase partition).

To the clear solution was added ammonium sulfate powder to be final concentration of 90%, and the resultant was repeatedly subjected to the triphase partition procedure to partition and obtain an intermediate protein aggregates layer between the tertiary butanol layer and the aqueous layer-(second triphase partition).

The protein aggregates were dissolved in a 20 mM sodium phosphate buffer(pH 6.8) and the solution was dialyzed sufficiently against the same buffer and passed over a S-Sepharose column(5 cm×10 cm, Pharmacia, Sweden) equilibrated with the same buffer. Then, the same buffer having a linear concentration gradient of 0M to 0.1M NaCl was added to the column to elute the aminopeptidase.

Eluted fractions showing the aminopeptidase activity were collected and then sufficiently dialyzed against a 20 mM sodium phosphate buffer(pH 6.8). The resulting solution was passed over a FPLC Mono-S column(0.5 cm×5 cm, Pharmacia, Sweden) equilibrated with the same buffer and the column was washed with the same buffer containing 0.3M NaCl. Then, the same buffer having a linear concentration gradient of 0.3M to 0.8M NaCl was added to the column to elute the aminopeptidase.

Example 4: Properties of the Novel Aminopeptidase

Properties of the novel aminopeptidase of the present invention were determined by the following various methods.

(1) Determination of the Molecular Weight

The molecular weight of the aminopeptidase obtained in Example 3 was determined by SDS-PAGE and the result is shown in FIG. 1, wherein:

lane 1 shows the standard molecular weight size marker proteins, i.e., 97, 67, 42, 31, 22 and 14 kilodaltons(kd) from the top of the gel;

lane 2 shows the aminopeptidase fraction eluted from the S-sepharose column; and lane 3 shows the finally purified aminopeptidase. As shown in the above result, molecular weight of the aminopeptidase obtained from the culture of *Streptomyces thermonitrificans* was about 41 to 45 kd when determined by SDS-PAGE.

In addition, molecular weight of the aminopeptidase in its natural state was determined by a gel filtration chromatography using a FPLC superose 12 column(1 cm×30 cm, Pharmacia, Sweden). A standard curve of the molecular weight as a function of the partition coefficient was obtained by eluting a recombinant human growth hormone(rhGH), an ovalbumin and a bovine serum albumin as standard proteins and then calculating the partition coefficients of the proteins according to the following equation:

$$\text{Partition coefficient} \approx \frac{\text{eluted volume} - \text{void volume}}{\text{total volume} - \text{void volume}}$$

Figure 2:
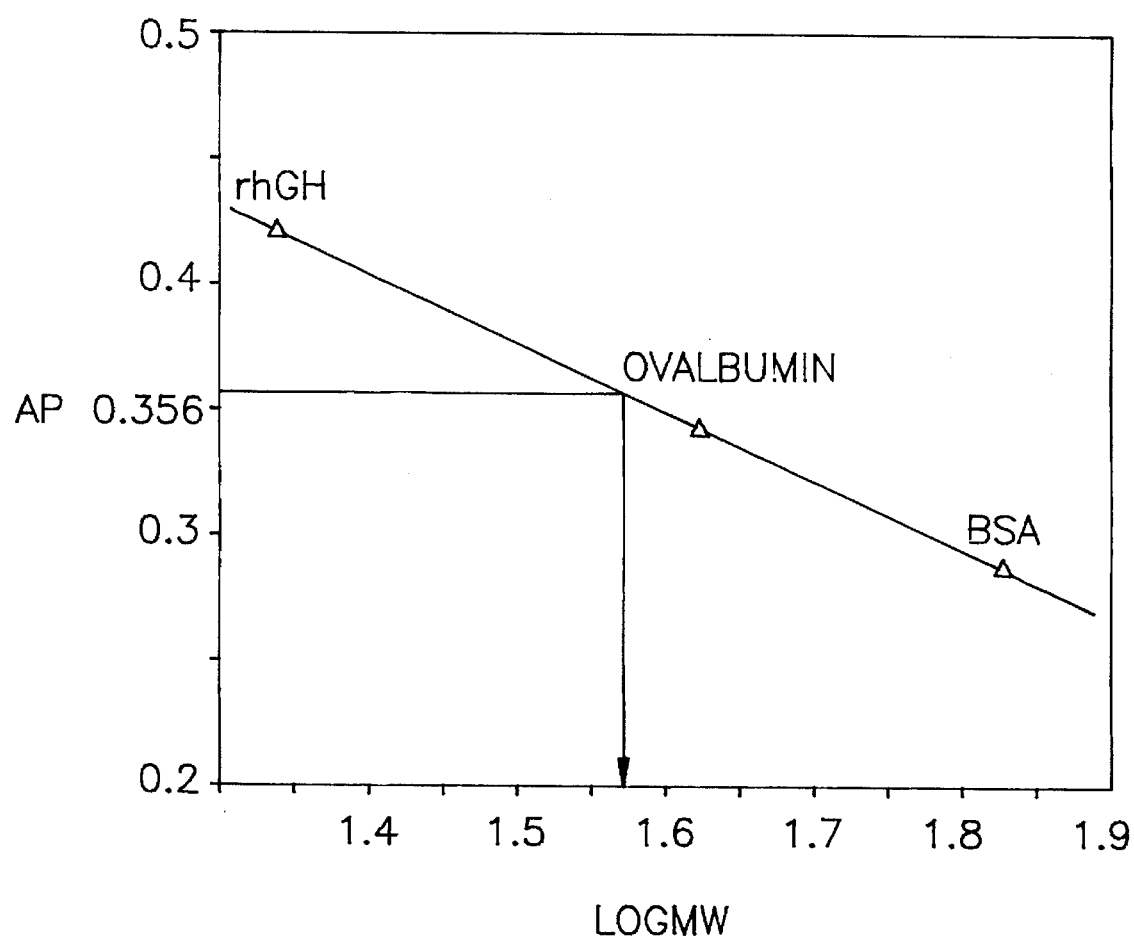
FIG. 2 depicts the result of gel filtration chromatography for determining the molecular weight of a natural (unreduced) form of the aminopeptidase.

The aminopeptidase obtained in Example 3 was eluted under the same condition as above to calculate its partition coefficient and then its molecular weight was determined with reference to the standard curve. As a result, it was confirmed that the molecular weight of the aminopeptidase of the present invention in its natural state is about 36 to 40 kd(FIG. 2).

(2) Amino Acid Sequence Analysis

N-terminal amino acid sequence of the aminopeptidase was analyzed in accordance with the automated Edman degradation reaction(Geoffrey Zubay, *Biochemistry*, 2nd ed., 47–48(1988)) by using an amino acid sequencer(model 471A, Applied Biosystems, U.S.A.). The resulting phenylthiohydantoin-attached amino acid residue was subjected to an HPLC by using a reversed phase HPLC column(220 mm×2.1 mm, model PTH-222, Applied Biosystems, U.S.A.). The retention time of each of phenylthiohydantoin-attached amino acid residues was measured and then compared with those of standard amino acid residues obtained by using that column. As a result, it was confirmed that N-terminal amino acid sequence of the aminopeptidase of the present invention is Lys-Phe-Ser-Lys-Lys-Phe-Asn-Glu (SEQ ID NO:3).

The internal amino acid sequence of the aminopeptidase of the present invention was confirmed by the following procedures.

Figure 3:
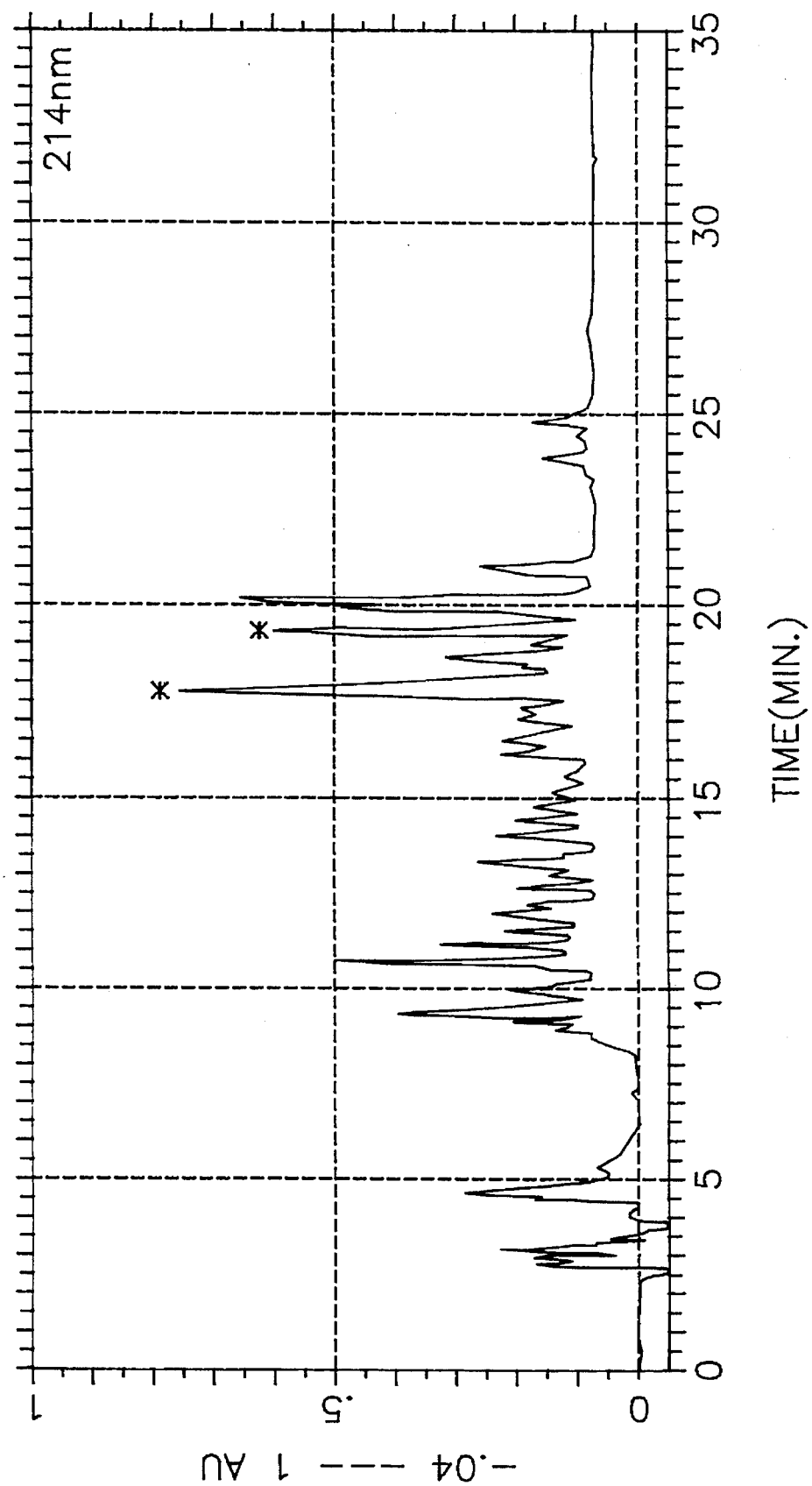
FIG. 3 represents the result of reversed phase high pressure liquid chromatography(HPLC) by using the trypsin-digested aminopeptidase for confirming the internal amino acid sequence thereof.

2 mg of the purified aminopeptidase was dissolved in 500 μl of ultrapure distilled water, boiled for 30 minutes to inactivate the aminopeptidase, lyophilized and then dissolved in 800 μl of 1 mM sodium hydroxide solution. To the solution were added 100 μl of 10X trypsin digestion buffer(1M Tris-Cl, 10 mM CaCl$_2$, pH 8.3) and 100 μl of 0.1 mg/ml trypsin(Boehringer Mannheim, Germany), and the mixture was reacted at 25° C. for 24 hours to digest the aminopeptidase completely. The peptides obtained in the reaction were passed over a reversed phase HPLC column(3.9 mm×300 mm, μBondapack C$_{18}$, Millipore, U.S.A.) to obtain a chromatogram(FIG. 3). The fractions corresponding to the peaks marked with * in FIG. 3 were collected and their amino acid sequences were confirmed in accordance with the method for analyzing N-terminal amino acid sequence as described above. As a result, it was found that the amino acid sequence of the peptide with retention time of 17.5 minute is Glu-Pro-Gly-Thr-Gly-Ala-Leu-Glu-Pro (SEQ ID NO:4) and that of the peptide with retention time of 19 minutes is Asn-Pro-Asp-Ile-Val-Tyr (SEQ ID NO:5).

(3) Determination of Optimum pH

Figure 4:
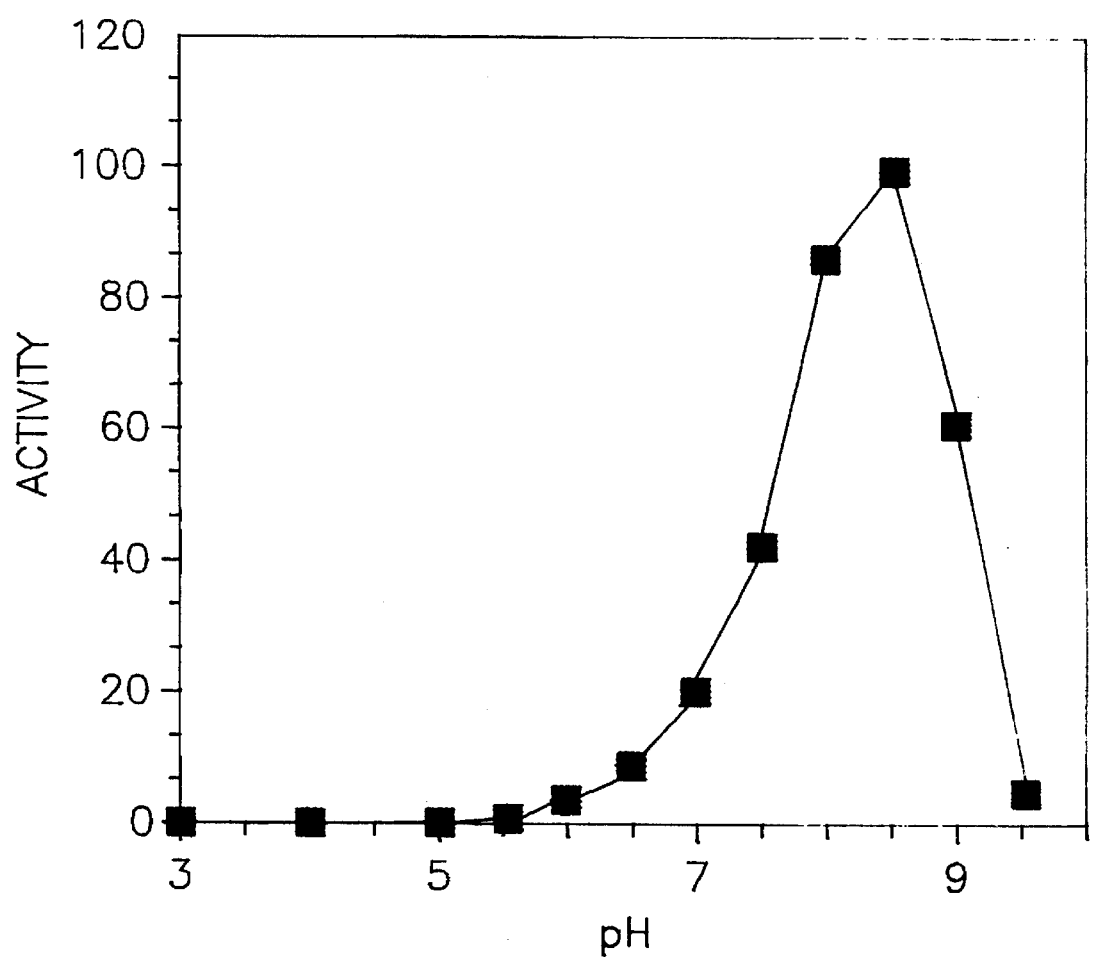
FIG. 4 illustrates the change in the activity of the aminopeptidase with respect to pH.

To determine the optimum pH for the activity of the aminopeptidase, its activities in an universal buffer(100 mM citric acid, 100 mM sodium phosphate, 100 mM boric acid and 100 mM phosphoric acid) containing 20 μl of 25 mg/ml leucine paranitroanilide dissolved in 50% DMSO, with a pH ranging from 3.0 to 9.5 were examined. The pH of the buffers were adjusted by using 5N sodium hydroxide. The result is shown in FIG. 4, wherein, it have been found that the pH for the activity of the aminopeptidase ranges from pH 7.5 to pH 9.0 and that the aminopeptidase is most active in the pH range of 8.0 to 8.5.

(4) Thermostability

Figure 5:
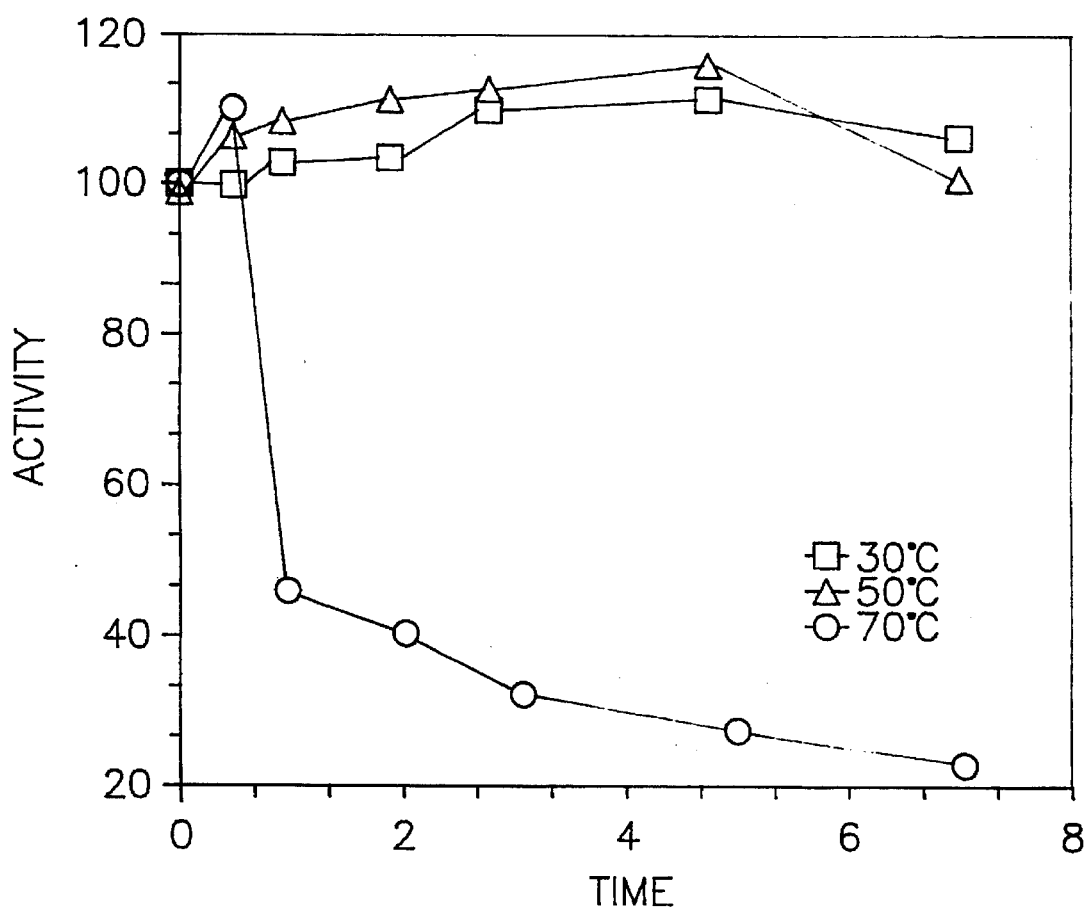
FIG. 5 demonstrates the change in the activity of the aminopeptidase with respect to temperature and time.

To confirm the thermostability of the aminopeptidase of the present invention, 18 tubes containing aliquots of the aminopeptidase prepared in Example 3 were allowed to stand at 30° C., 50° C. and 70° C. for 0.5, 1, 2, 3, 5 and 7 hours, respectively, and thereafter, activity of the aminopeptidase remains in each tube was determined in accordance with the method of the Reference Example. The result is shown in FIG. 5, wherein, it can be seen that the aminopeptidase is stable at 50° C. and 30° C.

(5) Effect of Orthophenanthroline on the Enzyme Activity

To confirm the effect of orthophenanthroline on the activity of the aminopeptidase, orthophenanthroline was added to the aminopeptidase fraction obtained in Example 3 to a final concentration of 0 mM, 1 mM and 5 mM, respectively. The resulting solution was reacted at 37° C. for 1 minute and then the activity of the aminopeptidase was determined. The result is shown in Table 2 below, and it is confirmed that the aminopeptidase of the present invention is a metallo-protease.

TABLE 2

| Effect of orthophenanthroline on the enzyme activity | |
|---|---|
| Concentration of orthophenanthroline (mM) | Activity(%) |
| 0 | 100 |
| 1 | 27 |
| 5 | 2 |

(6) Substrate Specificity

The substrate specificity of the aminopeptidase was examined as follows. Each 1 unit of the aminopeptidase was added to 100 mM Tris buffer(pH 8.0) containing 10 mM paranitroanilide of leucine, methionine, glycine-proline, alanine, lysine, glycine and glycine-phenylalanine, respectively, and the resulting mixtures were reacted at 37° C. The reaction time was regulated in accordance with the substrate so that paranitroanilide is produced in a fixed rate. The activities of the aminopeptidase according to the substrate were measured as in the Reference Example and compared with each other regarding the activity to leucine-paranitroanilide as 100%. The result is shown in Table 3 below.

TABLE 3

| Substrate specificity | |
|---|---|
| Substrate(10 mM) | Activity(%) |
| leucine-paranitroanilide | 100 |
| methionine-paranitroanilide | 3.60 |
| glycine-proline-paranitroanilide | 0.80 |
| alanine-paranitroanilide | 0.60 |
| lysine-paranitroanilide | 0.03 |
| glycine-paranitroanilide | 0.04 |
| glycine-phenylalanine-paranitroanilide | 0.11 |

Figure 6:
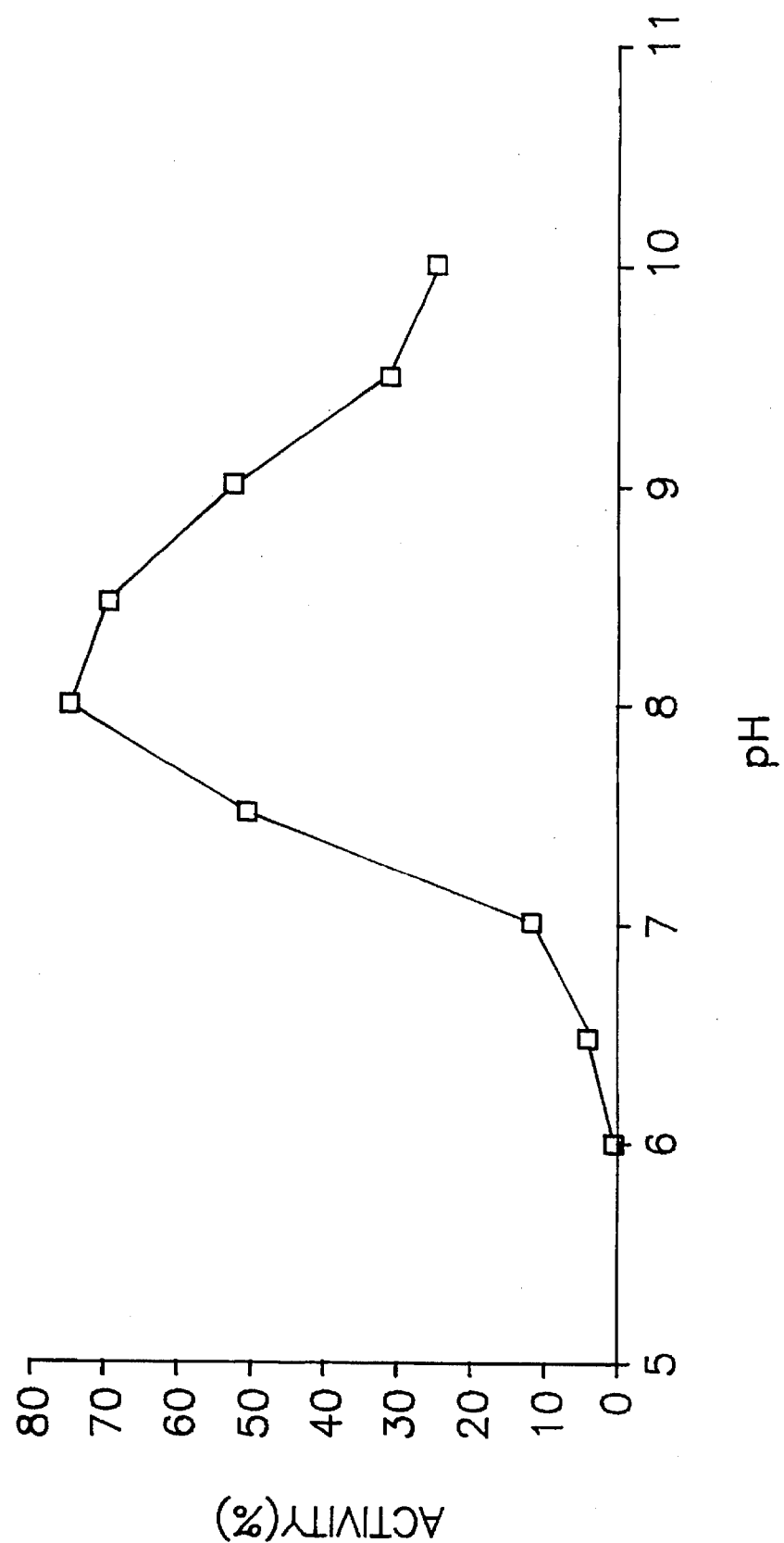
FIG. 6 describes the change in the level of activity of the aminopeptidase as a function of pH.

Example 5: Determination of Optimum Reaction Condition for Removing N-terminal Methionine of a N-methionyl Peptide 0.1M Tris buffers containing 200 μg of a N-methionyl peptide (Met-Phe-Pro-Thr-Glu-Pro-Ser) (SEQ ID NO:6) as a substrate and having the pH of 7, 7.5, 8, 8.5 and 9, respectively; 0.1M sodium phosphate buffers containing the same amount of the same substrate and having the pH of 6, 6.5, 7, and 7.5, respectively; and 0.1M sodium bicarbonate buffers containing the same amount of the same substrate and having the pH of 8.5, 9, 9.5 and 10, respectively, were prepared, and then, to 1 ml of each of the buffers was added 4.0 units of aminopeptidase. The mixtures were reacted at 37° C. for 10 minutes, and thereafter, the activity of the aminopeptidase in each reaction mixture was measured. The result is shown in FIG. 6, wherein the aminopeptidase shows high activity in a buffer having a pH of 7.5 to 9.5.

Figure 7:
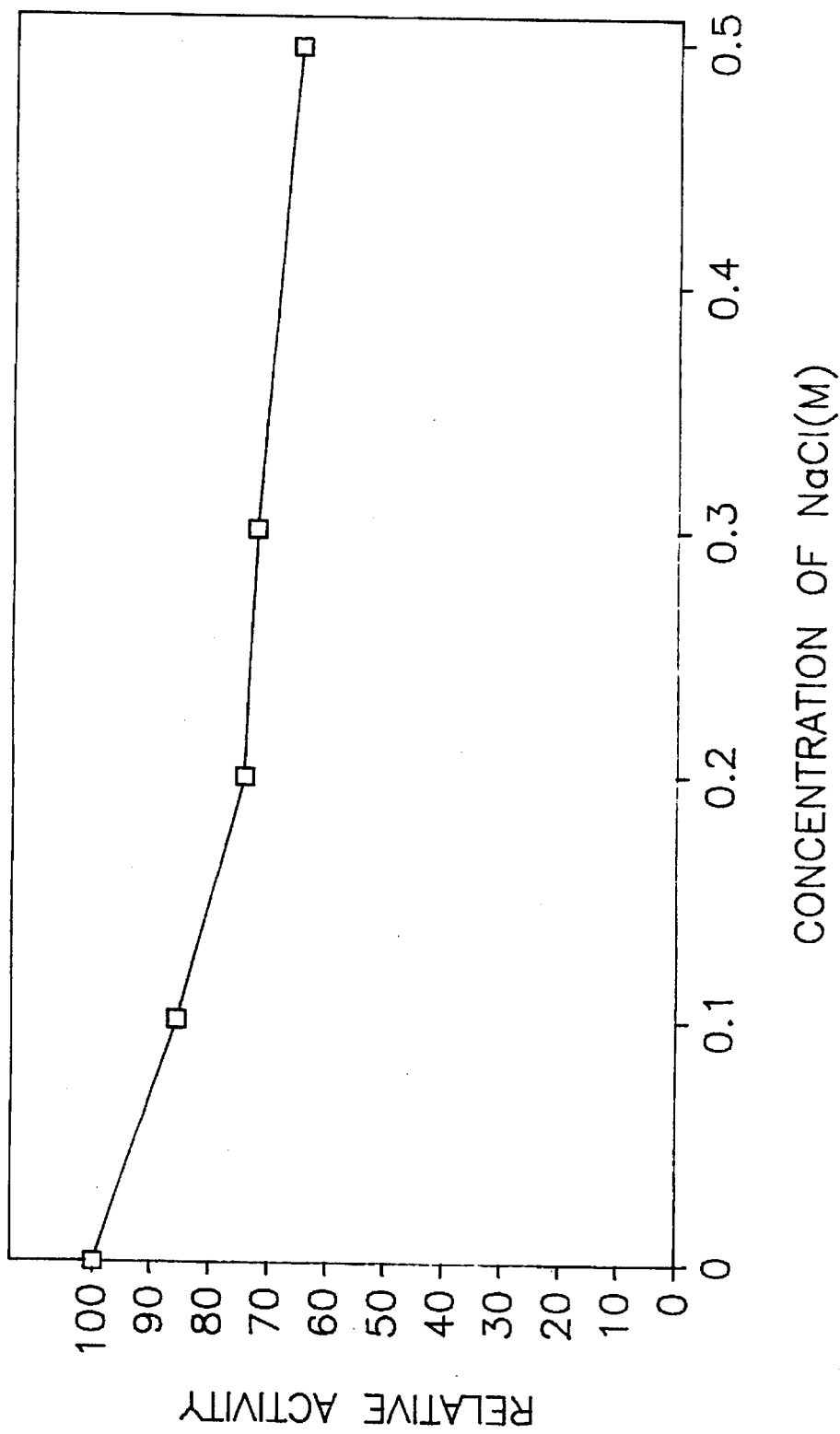
FIG. 7 is intended to explain the change in the relative activity of the aminopeptidase with respect to the concentration of sodium chloride in 100 mM Tris buffer(pH 8.0)

Further, the above substrate was treated with the aminopeptidase in a 100 mM Tris buffer(pH 8.0) containing NaCl to a final concentration of 0, 0.1, 0.2, 0.3, 0.4 and 0.5M, respectively, in order to confirm the optimum ionic strength to maintain the activity of aminopeptidase. The result is shown in FIG. 7, wherein the activity of aminopeptidase is decreased as the concentration of NaCl increases. However, since the ionic strength is necessary to maintain the stability of an enzyme for a long time, it is preferable to add NaCl to the reaction buffer to be 0 to 100 mM.

Example 6: Preparation of a Wild-Type Recombinant Human Growth Hormone 8 units of the aminopeptidase of the present invention was added to about 600 μg of a methionyl human growth hormone prepared in accordance with the method of Korean patent Publication No. 92–99 and the mixture was dialyzed sufficiently against a reaction buffer(50 mM Tris(pH 8.0), 100 mM NaCl and 1 mM PMSF). The dialyzate was concentrated to the volume of 0.6 ml by using a centricon (Amicon, U.S.A.) with 2 ml volume, and then, reacted in a water bath at 37° C. for 24 hours. After 24 hours, the reaction mixture was redialyzed sufficiently against 20 mM Tris buffer(pH 8.0), and then, passed over a DEAE-Sepharose column previously equilibrated with the same buffer. The column was washed with the same buffer and then a buffer containing 20 mM Tris and 100 mM NaCl was added to the column to elute the human growth hormone.

Example 7: Properties of a Wild-Type Recombinant Human Growth Hormone

Figure 8A:
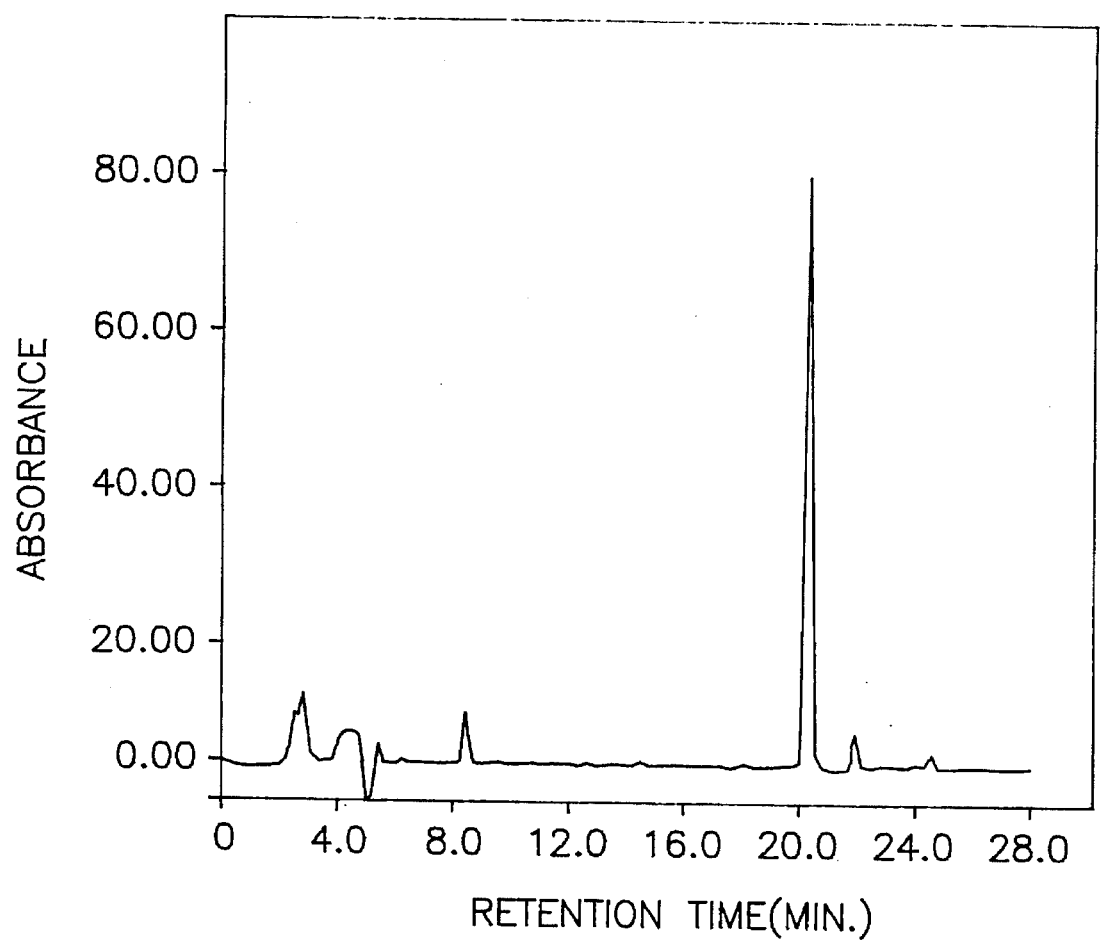
FIGS. 8A and 8B offer the results of an N-terminal amino acid analyses of a recombinant human growth hormone carried out before and after the removal of N-terminal methionine by using the aminopeptidase, respectively.
Figure 8B:
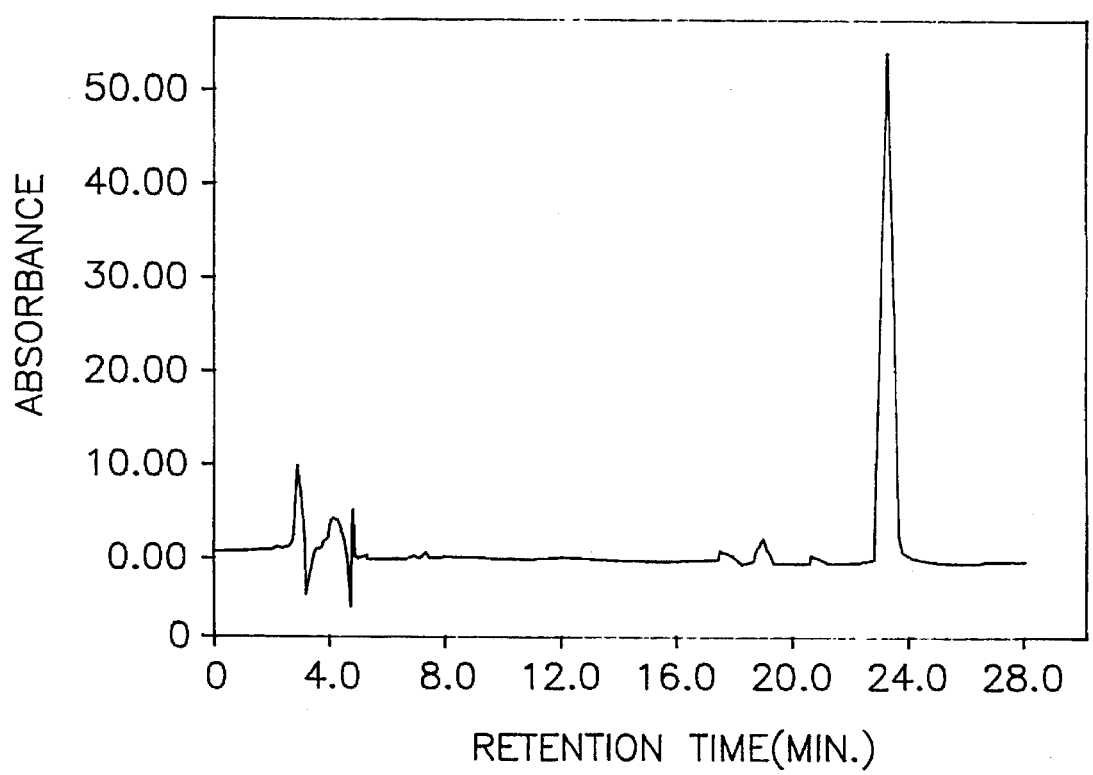

The removal of N-terminal methionine was confirmed by using the wild-type recombinant human growth hormone obtained in Example 6 with an N-terminal sequencer (Applied Biosystems, model 471A protein sequencer) and the results are shown in FIGS. 8A and 8B which represent the result of N-terminal sequencing before and after the aminopeptidase treatment, respectively. As can be seen from FIG. 8B, the first amino acid residue of the recombinant human growth hormone after the treatment with the aminopeptidase was disclosed as phenylalanine and methionine peak was rarely found. This result shows that the aminopeptidase of the present invention can remove specifically the N-terminal methionine residue from the recombinant human growth hormone.

Figure 9:
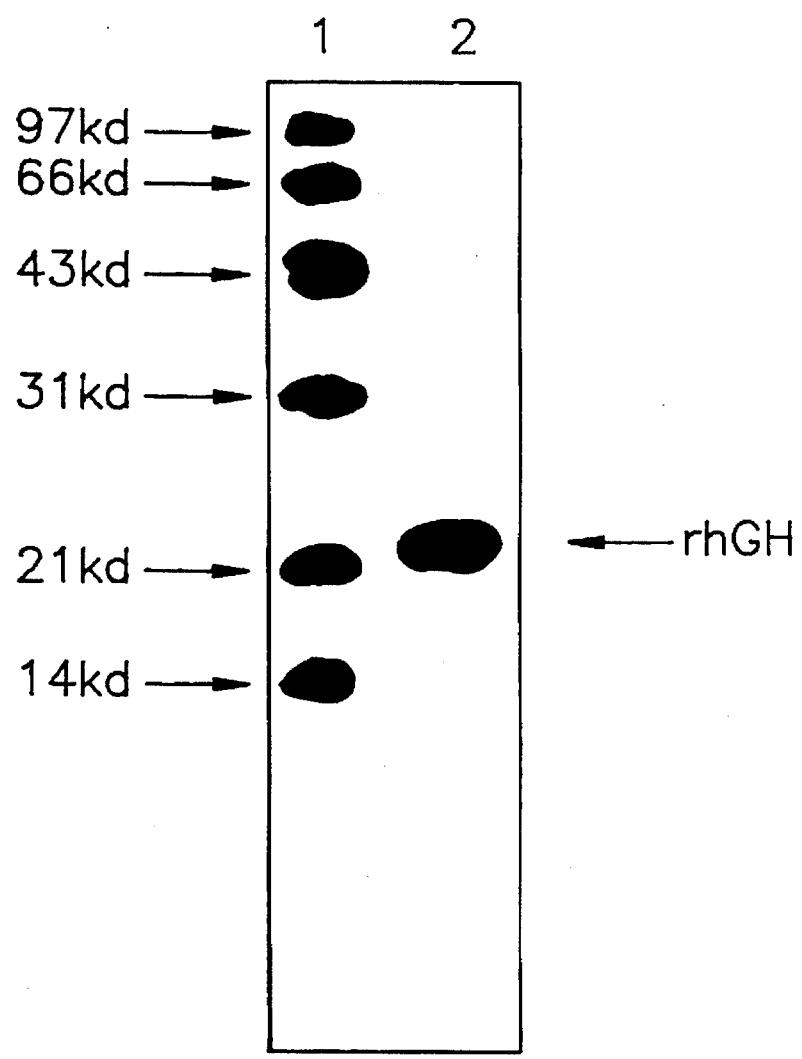
FIG. 9 presents the result of SDS-PAGE evidencing the purity of the wild-type recombinant human growth hormone prepared in accordance with the inventive process.

The purity of the wild-type recombinant human growth hormone was confirmed by SDS-PAGE and the result is shown in FIG. 9.

The potency of the finally purified wild-type recombinant human growth hormone was determined by a radio receptor assay (I. Tsushima and H. G. Frieson, *Journal of Clinical Endocrinology and Metabolism*, 37, 334(1973)) and, as a result, it has been found that the hormone has a potency of 2.7 IU/mg similar to 2.5 IU/mg which is the potency of pituitary gland-derived human growth hormone supplied by World Health Organization (WHO)(*Journal of Korean endocrinology society*, Vol. 5, No. 3(1990)).

While the invention has been described with respect to the above specific embodiments, it should be recognized that various modifications and changes may be made and also fall within the scope of the invention as defined by the claims that follow.

What is claimed is:

1. A substantially pure aminopeptidase isolated from a culture medium of *Streptomyces thermonitrificans*, said aminopeptidase being a $Zn^{2+}$-dependent metalloenzyme and comprising an amino acid sequence of Lys-Phe-Ser-Lys-Lys-Phe-Asn-Glu(SEQ ID NO: 3) at the N-terminal thereof and amino acid sequences of Glu-Pro-Gly-Thr-Gly-Ala-Leu-Glu-Pro(SEQ ID NO: 4) and Asn-Pro-Asp-Ile-Val-Tyr(SEQ ID NO: 5) at other regions thereof.

2. The aminopeptidase of claim 1 having an apparent molecular weight, as determined by sodium dodecyl sulfate polyacrylamide gel electrophoresis under a reducing condition, from 41 to 45 kd and an apparent molecular weight, as determined by gel filtration under a native state condition, from 36 to 40 kd.

3. The aminopeptidase of claim 1 having a pH optimum ranging from 7.5 to 9.0, and a temperature optimum ranging from 30° to 50° C.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) TOPOLOGY: linear ( i i ) MOLECULE TYPE: peptide ( i i i ) FRAGMENT TYPE: N-terminal ( i v ) ORIGINAL SOURCE:
    ( A ) ORGANISM: Streptomyces griseus ( v ) SEQUENCE DESCRIPTION: SEQ ID NO: 1:

Ala  Pro  Asp  Ile  Pro  Leu
    1                          5

( 2 ) INFORMATION FOR SEQ ID NO:2:

( i ) SEQUENCE CHARACTERISTICS:
    ( A ) LENGTH: 5 amino acids
    ( B ) TYPE: amino acid
    ( C ) TOPOLOGY: linear ( i i ) MOLECULE TYPE: peptide ( i i i ) FRAGMENT TYPE: N-terminal ( i v ) PROPERTIES: N-terminal of methionyl human growth hormone ( v ) SEQUENCE DESCRIPTION: SEQ ID NO: 2:

Met  Phe  Pro  Thr  Ile
    1                       5

( 2 ) INFORMATION FOR SEQ ID NO:3:

( i ) SEQUENCE CHARACTERISTICS:
    ( A ) LENGTH: 8 amino acids
    ( B ) TYPE: amino acid
    ( C ) TOPOLOGY: linear ( i i ) MOLECULE TYPE: peptide ( i i i ) FRAGMENT TYPE: N-terminal ( i v ) ORIGINAL SOURCE:
    ( A ) ORGANISM: Streptomyces thermonitrificans ( v ) SEQUENCE DESCRIPTION: SEQ ID NO: 3:

Lys  Phe  Ser  Lys  Lys  Phe  Asn  Glu
    1                          5

( 2 ) INFORMATION FOR SEQ ID NO:4:

( i ) SEQUENCE CHARACTERISTICS:
    ( A ) LENGTH: 9 amino acids
    ( B ) TYPE: amino acid
    ( C ) TOPOLOGY: linear ( i i ) MOLECULE TYPE: peptide ( i i i ) ORIGINAL SOURCE:
    ( A ) ORGANISM: Streptomyces thermonitrificans ( i v ) SEQUENCE DESCRIPTION: SEQ ID NO: 4:

Glu  Pro  Gly  Thr  Gly  Ala  Leu  Glu  Pro
    1                          5

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) TOPOLOGY: linear ( i i ) MOLECULE TYPE: peptide ( i i i ) ORIGINAL SOURCE:
    ( A ) ORGANISM: Streptomyces thermonitrificans ( i v ) SEQUENCE DESCRIPTION: SEQ ID NO: 5:

```
Asn  Pro  Asp  Ile  Val  Tyr
 1                 5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) TOPOLOGY: linear ( i i ) MOLECULE TYPE: peptide ( i v ) SEQUENCE DESCRIPTION: SEQ ID NO: 6:

```
Met  Phe  Pro  Thr  Glu  Pro  Ser
 1                 5
```